(12) United States Patent
Kohl et al.

(10) Patent No.: US 8,142,449 B2
(45) Date of Patent: Mar. 27, 2012

(54) DEVICE FOR INSERTING AT LEAST ONE ANCHOR PIECE INTO A HOLLOW SPACE OF A LIVING BEING

(75) Inventors: Thomas Kohl, Bonn (DE); Martin Oberlaender, Engen (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 459 days.

(21) Appl. No.: 11/848,275

(22) Filed: Aug. 31, 2007

(65) Prior Publication Data

US 2008/0071297 A1 Mar. 20, 2008

(30) Foreign Application Priority Data

Aug. 31, 2006 (DE) .......................... 10 2006 042 633

(51) Int. Cl.
*A61B 17/10* (2006.01)
(52) U.S. Cl. ................... 606/139; 606/144; 606/232
(58) Field of Classification Search .............. 606/108, 606/139, 142, 143, 144, 148, 151, 153, 156, 606/157, 213, 216, 217, 221, 232, 233; 604/174, 604/174.01, 175
See application file for complete search history.

(56) References Cited

U.S. PATENT DOCUMENTS

| 4,235,238 | A | * | 11/1980 | Ogiu et al. | 606/145 |
|---|---|---|---|---|---|
| 4,741,330 | A | * | 5/1988 | Hayhurst | 606/144 |
| 5,021,059 | A | * | 6/1991 | Kensey et al. | 606/213 |
| 5,085,661 | A | * | 2/1992 | Moss | 606/139 |
| 5,562,689 | A | * | 10/1996 | Green et al. | 606/151 |
| 5,626,614 | A | | 5/1997 | Hart | |
| 5,718,717 | A | * | 2/1998 | Bonutti | 606/232 |
| 5,861,004 | A | * | 1/1999 | Kensey et al. | 606/213 |
| 6,110,183 | A | | 8/2000 | Cope | |
| 6,972,027 | B2 | * | 12/2005 | Fallin et al. | 606/232 |
| 2001/0003158 | A1 | * | 6/2001 | Kensey et al. | 606/213 |

FOREIGN PATENT DOCUMENTS

WO 2005110280 A2 11/2005

OTHER PUBLICATIONS

European Search Report, EP07016790, Jul. 10, 2008, 9 pages.

\* cited by examiner

*Primary Examiner* — Ryan Severson
*Assistant Examiner* — David Eastwood
(74) *Attorney, Agent, or Firm* — St. Onge Steward Johnston & Reens LLC

(57) ABSTRACT

A device is used for inserting at least one anchor piece into a hollow space of a living being, in order to fix a wall of the hollow space temporarily to a wall of the body by means of the at least one anchor piece. It is proposed that the device has two shaft-like elements which are axially movable relative to one another and by which the at least one anchor piece is held captive at its axially spaced apart opposite ends, and moreover has an actuating mechanism via which the at least one element can be moved in such a way that the anchor piece held by it is released.

20 Claims, 7 Drawing Sheets

DEVICE FOR INSERTING AT LEAST ONE ANCHOR PIECE INTO A HOLLOW SPACE OF A LIVING BEING

RELATED APPLICATIONS

This application claims priority to German application 10 2006 042 633.9 filed on Aug. 31, 2006.

BACKGROUND OF THE INVENTION

The invention relates to a device for inserting at least one anchor piece into a hollow space of a living being, in order to fix a wall of the hollow space temporarily to a wall of the body of the living being by means of the at least one anchor piece.

The invention further relates to an anchor piece for use with the device according to the invention.

Such devices are used in the medical field for fixing the wall of a hollow space to the wall of the body during an examination or surgical intervention. They are used particularly in fetal diagnosis, therapy and surgery.

Fetal diagnosis, e.g. fetoscopy, involves examining a fetus using endoscopic methods.

To do this, a viewing instrument, namely a fetoscope, is passed through the abdominal wall of an expectant mother and into the amniotic sac. A physician is able to observe the fetus through the fetoscope. In addition to this viewing facility, fetoscopy also allows fetal samples (mostly skin) to be removed under visual control. The fetal sample removed can be diagnosed by means of special tests that are used to detect diseases during pregnancy.

It is hoped that fetal diagnosis, therapy and surgery will permit huge advances in the treatment of severe congenital abnormalities. However, the associated risks are enormous. The problems of the abovementioned examinations and surgical interventions are many. On the one hand, there is a possibility of the fetus, placenta or umbilical cord being damaged. On the other hand, any manipulation of the expectant mother's womb increases the risk of early labour and premature birth.

To avoid damage to the fetus, placenta or umbilical cord during an examination of the fetus or during a surgical intervention on the expectant mother's womb, more space must be created in the womb. In addition, the wall of the womb must be held stable and firm during the examination or the surgical intervention.

U.S. Pat. No. 5,085,661 discloses a fastener implanting device used to implant a head portion of a T- or H-shaped fastener within a body. The device has a needle portion and a grip portion. The needle portion has a head portion receiving cavity selectively covered by an axially movable sleeve. The sleeve's translational movement is controlled by a mechanism in the device's grip portion. When the sleeve is in a retracted position, the now uncovered head portion of the fastener can be released.

U.S. Pat. No. 5,626,614 discloses a surgical apparatus comprising a needle having an outer surface and an anchor bar disposed in sliding engagement within the needle. A pusher is movable coaxially of the needle to engage the anchor bar and to separate the anchor bar from the needle.

It is an object of the present invention to create a device that permits widening of the womb and holds the wall of the womb stable in this state.

It is a further object to create a device of slender shape for holding a strip-like anchor piece.

SUMMARY OF THE INVENTION

The object is achieved by a device for inserting at least one anchor piece into a hollow space of a living being, in order to fix a wall of said hollow space temporarily to a wall of a body of said human being by means of said anchor piece, comprising two shaft-like elements which are axially movable relative to one another, at least one anchor piece having two axially spaced apart opposite ends, said at least one anchor piece can be held captive between said two shaft-like elements at said axially spaced apart opposite ends, and an actuating mechanism via which at least one of said two shaft-like elements can be moved in such a way that said anchor piece held between said two shaft-like elements can be released.

The at least one anchor piece is held captive by the two shaft-like elements axially movable relative to one another, thus allowing the at least one anchor piece to be inserted safely, in a manner that requires little space, with the aid of the device according to the invention at a desired site in the expectant mother's womb.

This avoids the anchor piece falling out during the insertion of the device through the expectant mother's abdominal wall, which could lead to damage and unnecessary trauma to the abdominal wall and to the wall of the womb, but also to damage to the fetus, placenta and umbilical cord.

By virtue of this configuration of the device according to the invention, the anchor piece is released only after it has reached an end position in the womb, by actuation of the actuating mechanism.

By holding the strip-like anchor piece at is axially opposite ends no deep cavities have to be cut out in the shaft-like elements. This allows to design at least one of the shaft-like elements as a hollow shaft for inserting an additional instrument, for example a targeting wire.

To enlarge the womb space, the wall of the womb is extended, which leads to an increase in the size of the womb. With the aid of the anchor piece located in the womb and a thread connected thereon, the wall of the womb and the abdominal wall are joined firmly in one unit. To do this, the thread projecting the body of the human being is used to draw the wall of the womb outwards onto the inner face of the abdominal wall. Thereafter, an examination or a surgical intervention can be carried out on the enlarged womb of the expectant mother.

The shaft-like design of the two elements that hold the anchor piece allows the device to be inserted through a trocar, a standard instrument in minimally invasive surgery.

In another embodiment of the invention, the shaft-like elements are designed and arranged in such a way that a recess is formed in which the at least one anchor piece can be held.

This measure has the advantage of affording the possibility of a strip-like anchor piece being received in the recess formed between the two shaft-like elements. This allows the device to have a slender structure that takes up little space.

In another embodiment of the invention, the actuating mechanism has an actuating element for moving at least one of the shaft-like elements, where, in a first position of the shaft-like elements, the at least one anchor piece is held captive in the recess, and, in a second position of the shaft-like elements, the at least one anchor piece can be fitted or released.

This measure has the advantage that the shaft-like elements can be brought into the first position or into the second position by a simple actuation of the actuating element.

In another embodiment of the invention, the actuating mechanism has a spring which acts on the at least one shaft-like element in such a way that the shaft-like elements are brought into the first position.

This measure has the advantage that the shaft-like elements are permanently acted upon by a spring force in the direction of the first position, i.e. into the position in which the at least one anchor piece is held captive between the shaft-like elements. This has the effect that the at least one anchor piece is permanently held captive between the spring-loaded, shaft-like elements.

In another embodiment of the invention, the actuating element, upon actuation counter to the force of the spring, moves the shaft-like elements in such a way that they are brought into the second position, and that, upon release of the actuating element, the shaft-like elements are brought back to the first position.

This measure has the advantage that, because the at least one shaft-like element is spring-loaded, the shaft-like elements are brought automatically from the second position to the first position when the actuating element is let go. This simplifies the handling of the device, since, without actuation, the anchor element is permanently held secure.

In another embodiment of the invention, a head is arranged on a proximal end of the shaft-like elements.

This measure has the advantage that the device can be securely and firmly gripped by a human hand via the head, which is located at the proximal end of the shaft-like elements and therefore remains outside the patient's body during the examination or the surgical intervention.

In another embodiment of the invention, the actuating element is designed as a push-button arranged on the head.

This measure has the advantage that the actuating element designed as a pushbutton can be actuated by a finger, for example the thumb, of the hand that is holding the device. The device according to the invention can therefore be held and also actuated with just one hand.

In another embodiment of the invention, the actuating element is movable in the direction of the axial movement of the shaft-like elements.

This embodiment too leads to ergonomic handling of the device according to the invention with just one hand.

In another embodiment of the invention, one of the shaft-like elements is designed as an outer tube, and the other is designed as an axially displaceable inner shaft received in the outer tube.

This measure has the advantage that such a design of the shaft-like elements permits a compact and yet stable device which, while having very small dimensions overall, has the required stability.

In another embodiment of the invention, the inner shaft is pressed by means of the spring in the direction of the head.

This measure has the advantage that the spring-loaded inner shaft, which is pressed in the direction of the head, ensures a secure fit of the at least one anchor piece held between the inner shaft and the outer tube. This means that if the inner shaft comes up against anything, it is not inadvertently moved in such a way that the anchor piece is released.

In another embodiment of the invention, the inner shaft is operatively connected to the actuating mechanism in such a way that an actuation of the actuating element causes an axial displacement of the inner shaft along a longitudinal axis.

This measure has the advantage that the actuation of the actuating element, designed as the push-button, can be converted in a mechanically simple way into an axial displacement of the inner shaft.

In another embodiment of the invention, the distal end of the inner shaft is designed as a tip.

This measure has the advantage that the operating surgeon can precisely target the point of application by way of the tip. It also permits gentle insertion of the device through the abdominal wall into the womb or into a trocar.

In another embodiment of the invention, the shaft-like elements each have a jaw between which the at least one anchor piece is held captive.

This measure has the advantage that the jaws between which the at least one anchor piece is held captive ensure a particularly secure fit of the at least one anchor piece.

In another embodiment of the invention, one jaw is arranged on the distal end of the outer tube, and the other jaw is arranged on the proximal end of the tip of the inner shaft.

Such an arrangement of the jaws means that the recess in which the at least one anchor piece can be held is limited on both sides by the jaws. The jaws serve as an orientation feature during introduction of the anchor element and they permit visual control of the exact fit of the anchor element.

In another embodiment of the invention, each jaw has at least one pocket.

This measure has the advantage that, by virtue of such a configuration of the invention, the at least one anchor piece is held at its axially opposite ends securely in the pockets of the jaws in such a way that radial displacement of the anchor piece is ruled out.

In another embodiment of the invention, the recess is designed in such a way that two radially opposite anchor pieces can be held in it.

This measure has the advantage that two anchor pieces can be introduced simultaneously into the womb. This allows the wall of the womb to be widened out and fixed at two different places on the abdominal wall.

In another embodiment of the invention, a mechanism for application of a trocar is arranged on the head.

This measure has the advantage that a trocar can be fixed to the device according to the invention, by means of which trocar an opening can be created in the abdominal wall and in the wall of the womb and through which the device can be inserted into the body.

In another embodiment of the invention, an ejection mechanism is provided for ejecting the at least one anchor piece.

This measure has the advantage that, if the anchor piece becomes jammed or blocked by surrounding tissue, the ejection mechanism ensures that the anchor piece is released from the device according to the invention.

According to the invention, the object is also achieved by the fact that an anchor piece has a body designed in the form of a strip.

This measure has the advantage that the anchor piece according to the invention can be placed tightly on the shafts holding it.

In another embodiment of the invention, the strip-shaped body has the geometry of the section of an outer tube.

This measure has the advantage that the anchor piece according to the invention does not protrude radially from the outer tube, but instead can be received completely within the recess. Thus, the device according to the invention can be inserted with the at least one anchor piece into a shaft of the trocar.

In another embodiment of the invention, the anchor piece is rounded at both ends.

This measure has the advantage that such a configuration of the anchor piece rules out the possibility of the wall of the womb being damaged by sharp corners or edges.

In another embodiment of the invention, the anchor piece is provided with at least one approximately central opening for engagement of a draw-thread.

This measure has the advantage that the draw-thread, which is routed out of the abdominal wall, can be used to easily manoeuvre the anchor piece, i.e. to place it first against the inner face of the womb. After the wall of the womb has been drawn up, the widened womb is fixed on the abdominal wall of the patient. To do this, the end of the draw-thread protruding outside the body is pulled, and it is then fixed on the body, for example by a clip. Thus, the wall of the womb and the abdominal wall form a firmly connected unit.

In another embodiment of the invention, the anchor piece is provided with at least one end opening for engagement of a retrieval thread.

This measure has the advantage that, with the aid of the retrieval thread, which is located inside the womb, the anchor piece can be removed again from the body after the examination or the surgical intervention.

In another embodiment of the invention, the draw-thread and the retrieval thread of the anchor piece held captive on the device can be arranged in the interior of a shaft of a trocar.

This measure has the advantage that, by arranging the two threads in the trocar shaft, the threads do not impede the insertion of the device through the abdominal wall into the womb and are also themselves not impeded.

In another embodiment of the invention, the draw-thread and the retrieval thread of the anchor piece held captive on the device can be arranged outside the shaft of a trocar.

This measure has the advantage that if the threads do not fit into the trocar shaft, because of the size of the particular trocar, they can be arranged outside of the trocar shaft during insertion of the device into the womb.

It will be appreciated that the aforementioned features and those still to be explained below can be used not only in the cited combinations, but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which.

DETAILED DESCRIPTION OF PREFERRED EMBODIMENTS

A device shown in the figures, and used for inserting at least one anchor piece into a hollow space of a living being, is designated in its entirety by reference number 10.

Figures 1, 2:
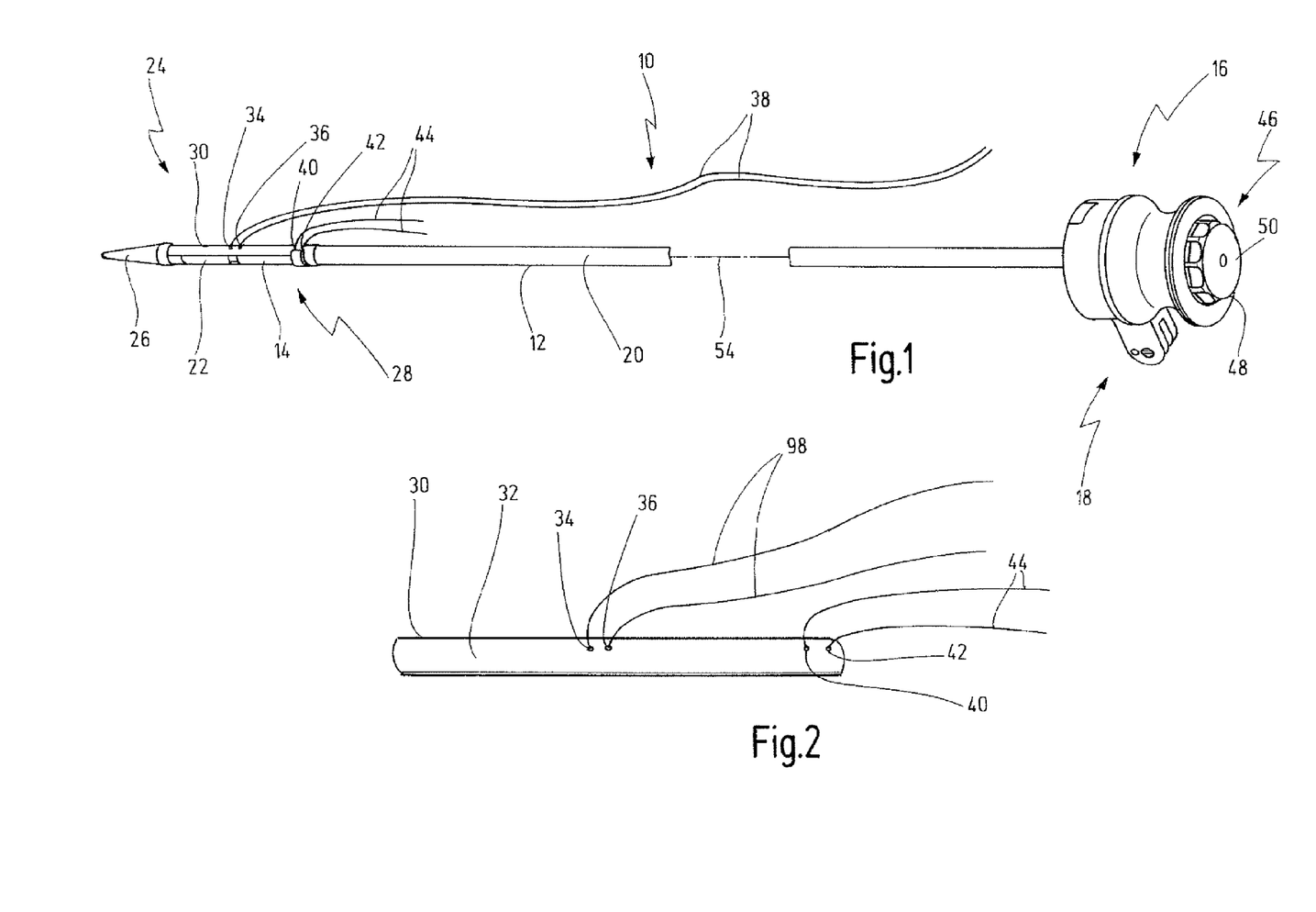
FIG. 1 shows a perspective side view of a device according to the invention.
FIG. 2 shows an enlarged view of an anchor piece from FIG. 1.

As is evident in particular from FIG. 1, the device 10 according to the invention has two shaft-like elements 12, 14, on whose proximal end 16 a head 18 is arranged. The shaft-like elements 12, 14 are movable relative to one another.

In this illustrative embodiment, one of the shaft-like elements 12 is designed as an outer tube 20. The other shaft-like element 14, by contrast, is designed as an inner shaft 22 received in the outer tube 20.

A distal end 24 of the inner shaft 22 is designed as a tip 26, which makes it easier to target and insert the device 10 according to the invention through the abdominal wall and into the womb.

Figure 4:
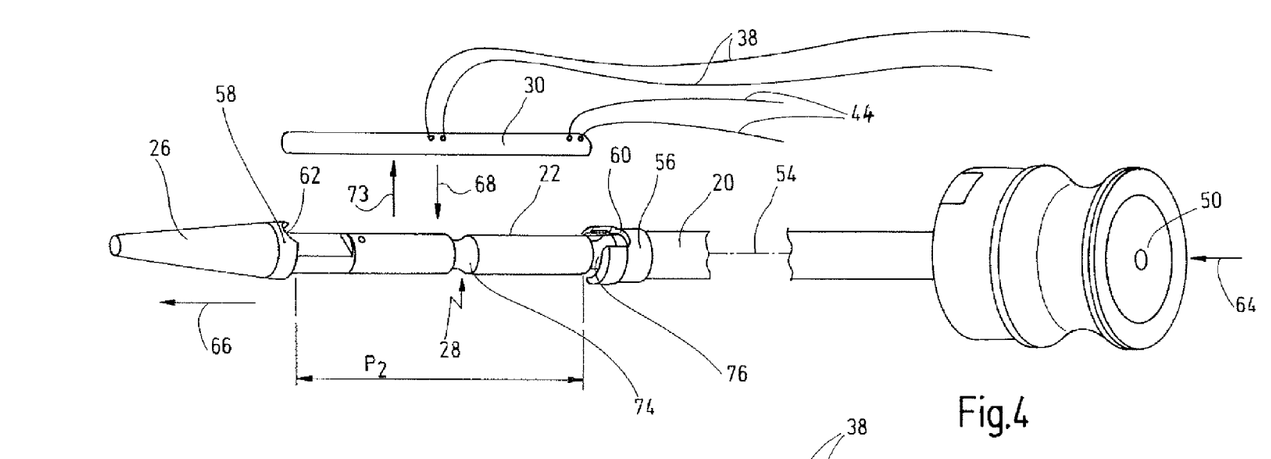
FIG. 4 shows an enlarged perspective side view of the device according to the invention, prior the anchor piece is fitted.

A recess 28 is formed between the distal end of the outer tube 20 and the distal end of the inner shaft 22, as can be seen in particular from the enlarged view in FIG. 4.

An anchor piece 30 can be received in the recess 28.

The anchor piece 30 has a strip-shaped body 32 (see also FIG. 2).

The body 32 is designed in the form of a tube section, the geometry of which corresponds to the geometry of the outer tube 20. The anchor piece 30 is rounded at both of its opposite ends.

The anchor piece 30 has two central openings 34, 36 through which a draw-thread 38 is engaged. In addition, the anchor piece 30 has two end openings 40, 42, which are arranged on one end section of the anchor piece 30. A retrieval thread 44 is engaged through the end openings 40, 42.

The draw-thread 38, which is markedly longer than the retrieval thread 44, is used to fix the wall of the womb on the abdominal wall. By contrast, the shorter retrieval thread 44 is used to remove the anchor piece 30 at the end of the examination or of the surgical intervention, as will be described below.

The inner shaft 22 has two depressions 74, 76, which are arranged at the location where the central openings 34, 36 and the end openings 40, 42 of the anchor piece 30 come to lie. The threads 38, 44 can be fitted in these depressions 74, 76.

The device 10 according to the invention has an actuating mechanism 46 via which one of the shaft-like elements 12, 14 can be moved in such a way that the anchor piece 30 held by it is released.

The actuating mechanism 46 has an actuating element 48, which is arranged on the head 18.

In this illustrative embodiment, the actuating element 48 is designed as a pushbutton 50 that can be moved in the direction of the axial movement of the shaft-like elements 12, 14.

Figure 3:
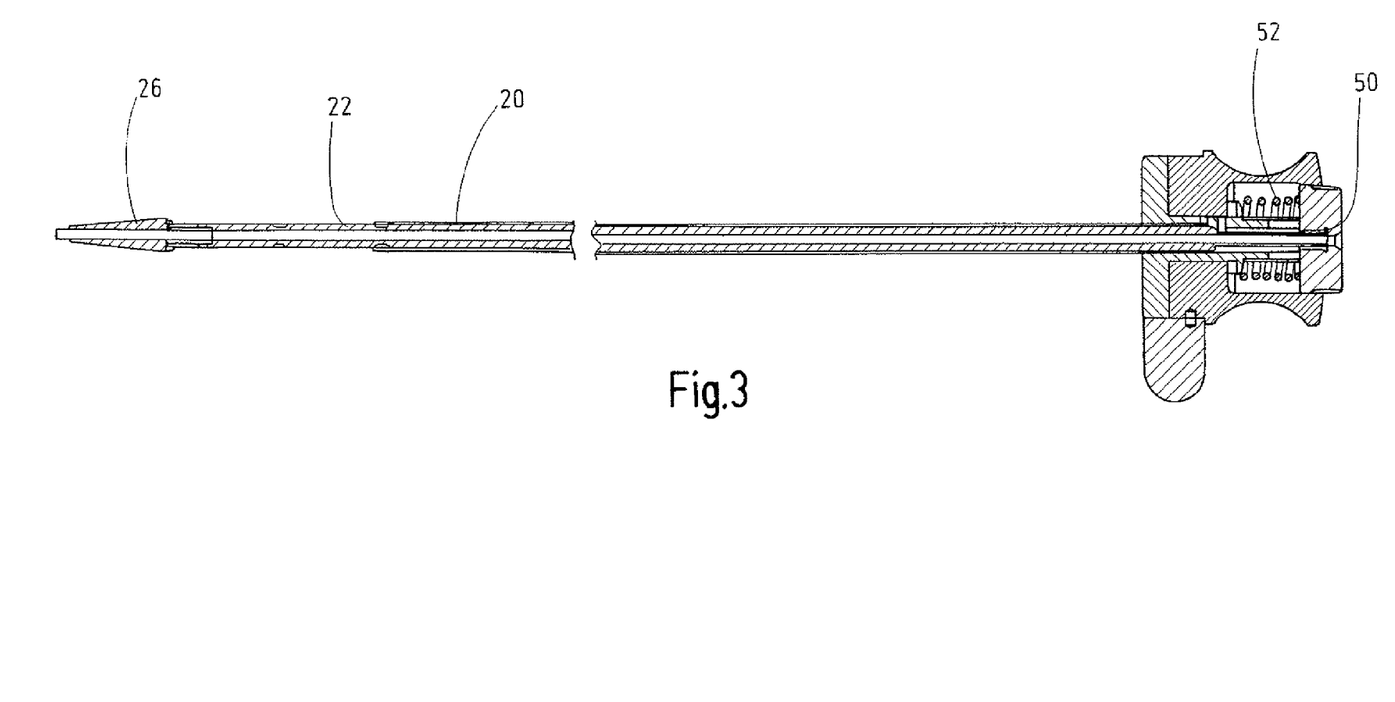
FIG. 3 shows a section, along a longitudinal axis, of FIG. 1, with no anchor piece held between the shaft-like elements.

The actuating mechanism 46 has a spring 52, as can be seen from the cross section along a longitudinal axis 54 in FIG. 3.

The spring 52 acts on the inner shaft 22, specifically in such a way that the inner shaft 22 is forced by means of the spring 52 in the direction of the head 18. When the push-button 50 is pressed, the inner shaft 22 is displaced in the distal direction. From the sectional view of FIG. 3 it appears that inner shaft 22 is a hollow shaft allowing to insert for example a targeting wire protruding the tip 26

Figure 5:
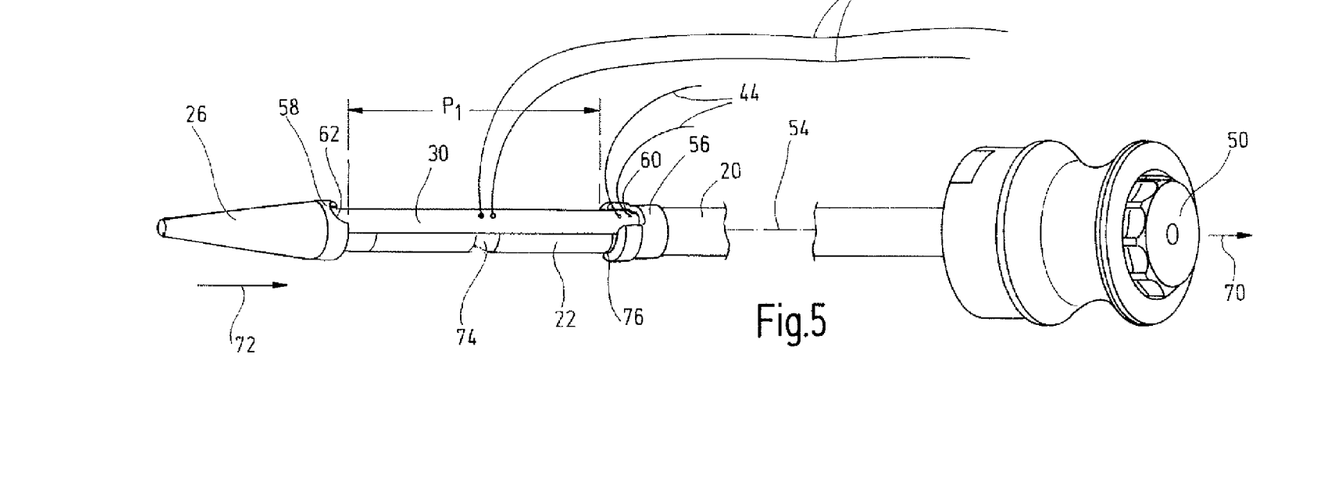
FIG. 5 shows a view comparable to the view in FIG. 4, with the anchor piece held between the shaft-like elements.

It will be seen from the enlarged perspective side views in FIGS. 4 and 5 that jaws 56, 58 are formed respectively at the distal end of the outer tube 20 and at the proximal end of the tip 26 formed on the distal end of the inner shaft 22. Each jaw 56, 58 has a respective pocket 60, 62. The pocket 60 formed at the distal end of the outer tube 20 lies exactly opposite the pocket 62 formed at the proximal end of the tip 26. The mutually opposite pockets 60, 62 avoid a radial displacement of the anchor piece 30, which can be held between the jaws 56, 58. The shape of the pockets corresponds to the round configuration of the rounded ends of the anchor piece 30.

The actuation of the actuating element 48 designed as the push-button 50, which in this illustrative embodiment is done by pressing the push-button 50 and is indicated by an arrow 64 in FIG. 4, causes an axial displacement of the inner shaft 22 along the longitudinal axis 54. The axial displacement is indicated by an arrow 66.

By means of the axial displacement of the inner shaft 22, the two shaft-like elements 12, 14, namely the outer tube 20 and the inner shaft 22, are brought into a second position $P_2$. The second position is defined as a distance between the two jaws 56, 58 that is greater than the length of the anchor piece 30.

In the second position $P_2$, the anchor piece 30 can be fitted in the recess 28 formed between the jaws 56, 58. The placement of the anchor piece 30 is indicated by an arrow 68.

After the anchor piece 30 has been fitted in the recess 28, the inner shaft 22 spring-loaded by the spring 52 (see FIG. 3) automatically moves in the direction of the proximal end 16 of the device 10 after the push-button 50 has been let go (arrow 70, FIG. 5). The proximal movement of the inner shaft 22 is indicated in FIG. 5 by an arrow 72.

In this way, the shaft-like elements 12, 14 are brought into a first position $P_1$. In this position, the anchor element 30 is held captive between the jaws 56, 58.

To release the anchor piece 30 again, the two shaft-like elements 12, 14 have to be brought into the second position $P_2$ by pressing the push-button 50 (see arrow 64, FIG. 4). The anchor piece 30 is released as indicated by an arrow 73 in FIG. 4.

Figure 6:
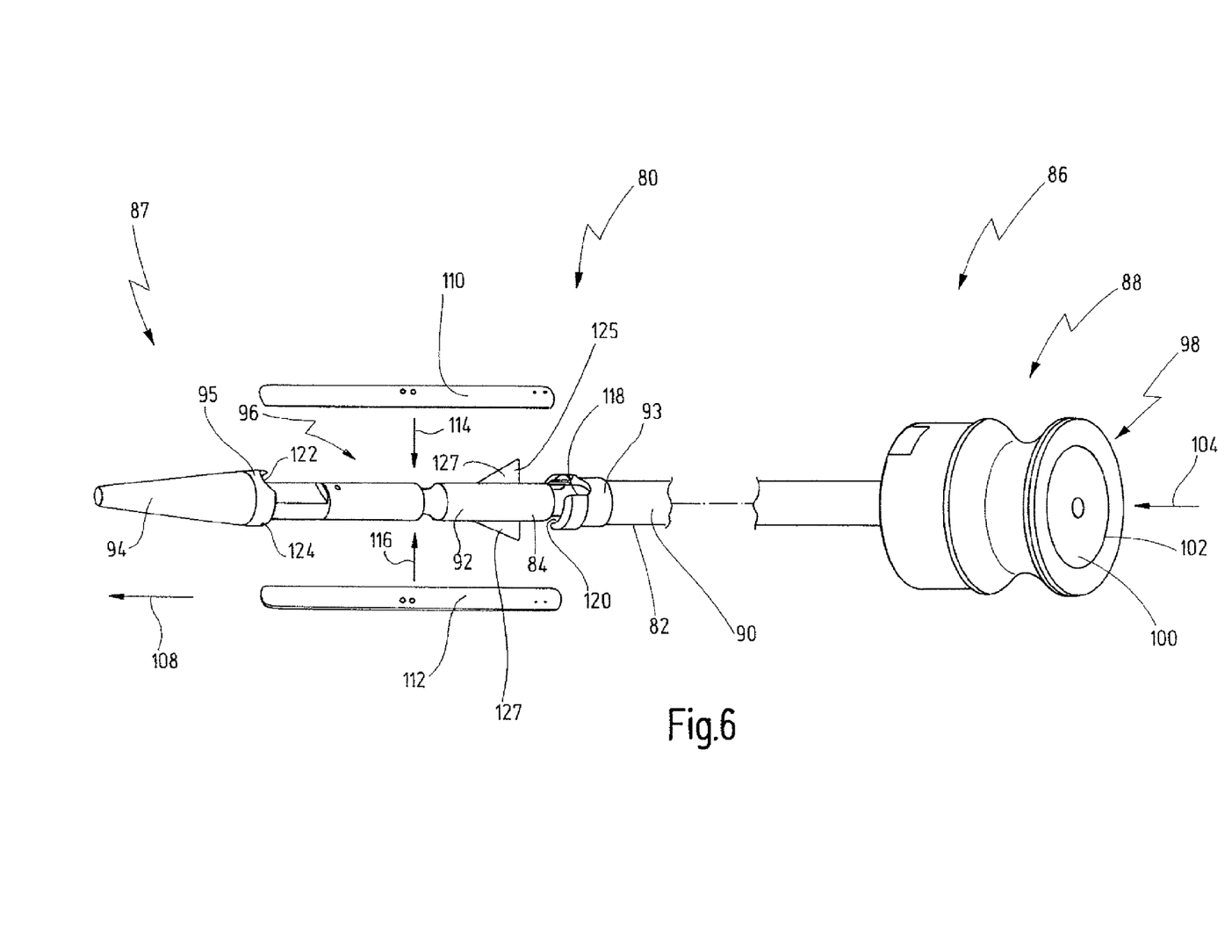
FIG. 6 shows another illustrative embodiment, in a view comparable to the view in FIG. 4, with two anchor pieces being able to be fitted.

FIG. 6 shows an illustrative embodiment 80 of the device according to the invention that differs from the illustrative embodiment of FIG. 4 in terms of the number of anchor pieces that can be held between the shaft-like elements.

In the illustrative embodiment shown in FIG. 6, the device 80 has two similarly shaft-like elements 82, 84, at whose proximal end 86 a head 88 is arranged.

One of the shaft-like elements 82 is similarly designed as an outer tube 90 and the other shaft-like element 84 is designed as an axially movable inner shaft 92 received in the outer tube 90.

A distal end 87 of the inner shaft 92 is similarly designed as a tip 94.

A recess 96 is similarly formed between the distal end of the outer tube 90 and the distal end of the inner shaft 92.

Jaws 93, 95 are arranged, respectively, at the distal end of the outer tube 90 and at the proximal end of the tip 94.

The device 80 likewise has an actuating mechanism 98, which likewise has an actuating element 102 designed as a push-button 100.

Compared to the illustrative embodiment from FIG. 4, it will be seen that, in the device 80, two mutually opposite anchor pieces 110, 112 can be fitted.

In contrast to the illustrative embodiment from FIG. 4, each jaw 93, 95 has two mutually opposite pockets 118, 120; 122, 124.

The actuating mechanism 98 is actuated in the same way as in the first illustrative embodiment shown in FIG. 4.

Pressing the push-button 100, as indicated by an arrow 104, causes an axial displacement along a longitudinal axis 106 of the inner shaft 92 (see arrow 108). The shaft-like elements 82, 84 are thus brought into the second position $P_2$.

In the second position $P_2$, the two anchor pieces 110, 112 are fitted into the recess 96. The placement of the two anchor pieces 110, 112 is indicated by arrows 114, 116.

Figure 7:
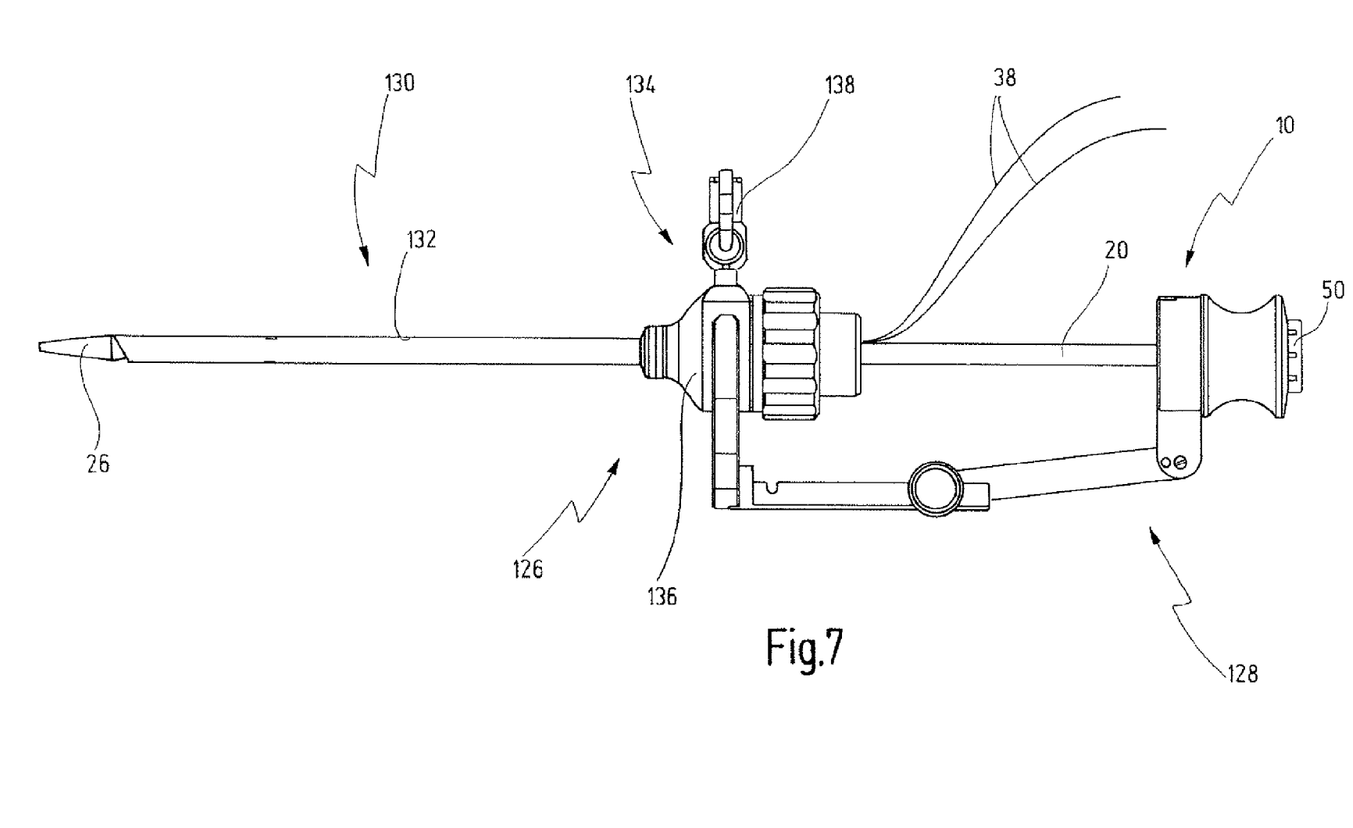
FIG. 7 shows a side view of a device according to the invention on which a trocar is mounted, the device being pushed partially into the trocar sleeve.

FIG. 7 shows a side view of the device 10 on which a trocar 126 is fixed by means of a mechanism 128. Trocars are used to insert medical instruments from the outside into the body through an incision.

The trocar has a trocar sleeve 130 with a shaft 132 at whose proximal end a housing 134 is arranged. The housing 134 has an approximately hollow cylindrical outer section 136, which directly adjoins the proximal end of the hollow shaft 132. A connector piece 138 protrudes radially from the outer section 136. A gas can be conveyed via the connector piece 138 into the interior of the housing 134 and through the shaft 132.

In this illustrative embodiment shown in FIG. 7, the draw-thread 38 and the retrieval thread 44 (not shown here) are arranged in the interior of the shaft 132 of the trocar 126.

The use of the device 10 according to the invention will be explained in brief with reference to FIGS. 8 and 9.

The shaft-like elements and the inserted anchor piece (or pieces) are introduced directly, or via a trocar, through the abdominal wall 140 and the wall 144 of the womb into the interior of the womb 142. This can be done under endoscopic observation. If a targeting wire is inserted into the hollow inner shaft the location of insert at the abdominal wall 140 can be targeted.

Figure 8:
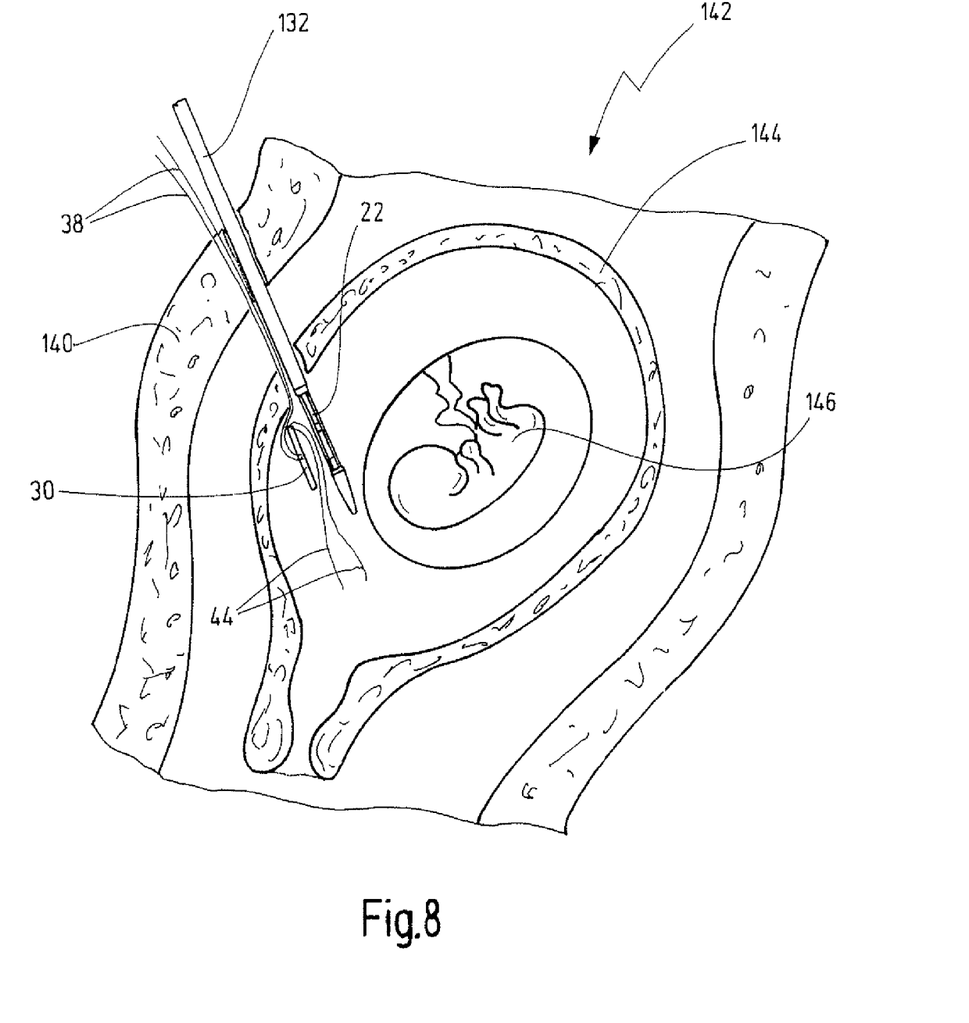
FIG. 8 shows a cross section through the lower abdomen of a pregnant patient in the area of the vagina and womb, the device according to the invention having been inserted into the womb by way of the abdominal wall, and the anchor piece having been released from the device according to the invention.

FIG. 8 shows a situation in which the anchor piece 30 has already been released.

It will be seen from this figure that the draw-thread 38 of the anchor piece 30 located in the womb 142 is routed outwards from the abdominal wall 140 of the patient. The retrieval thread 44, by contrast, is located in the womb 142.

Figure 9:
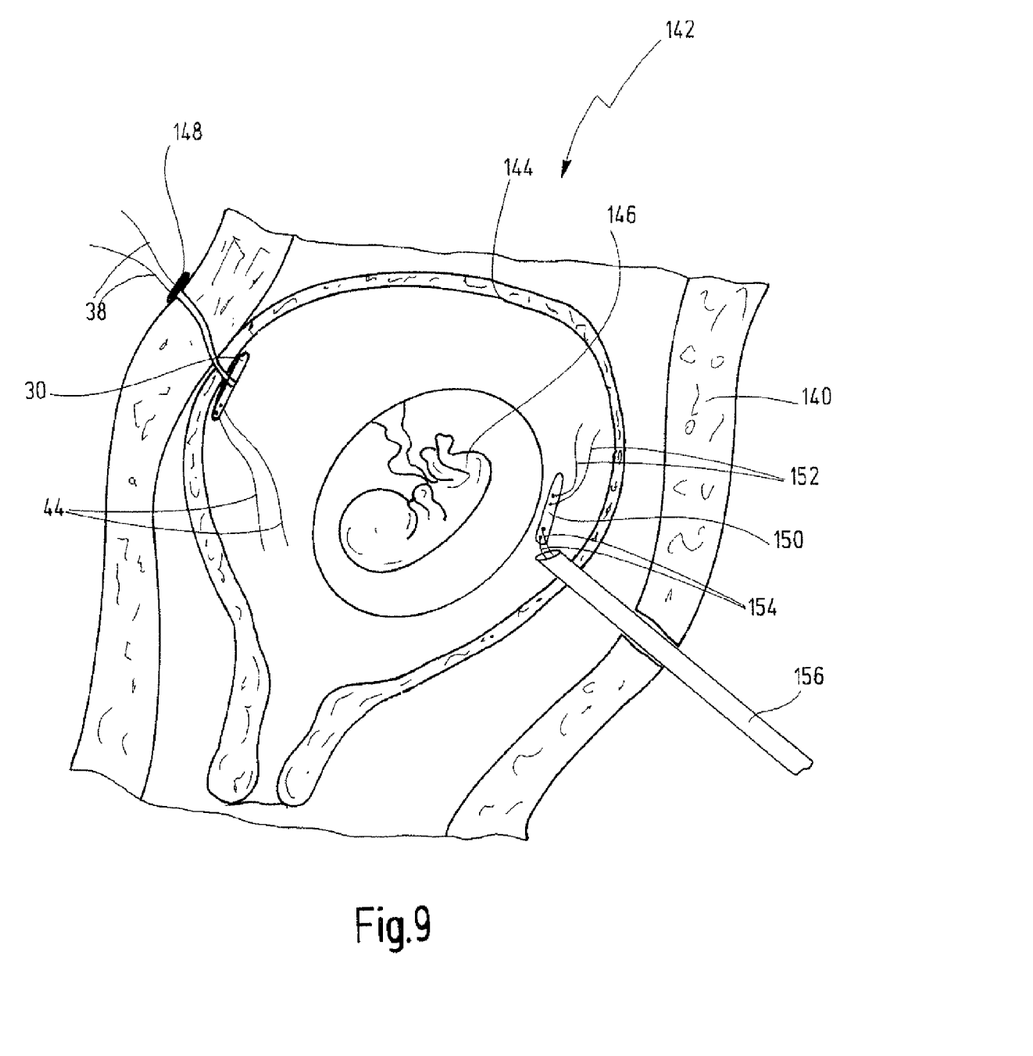
FIG. 9 shows a cross-sectional view comparable to the cross-sectional view in FIG. 8, the wall on one side of the womb being fixed to the abdominal wall, and the retrieval of an anchor piece being depicted on the other side of the womb.

The device 10 is thereafter removed from the womb 142, and the wall 144 of the womb is drawn onto the inside face of the abdominal wall 140 by means of the anchor piece 30 located in the womb 142 and by means of the draw-thread 38 engaged through the anchor piece 30, and the draw-thread is fixed from outside the abdominal wall 140 with a clip 148 (FIG. 9, left).

It will be seen from the view in FIG. 9 that drawing the wall 144 of the womb onto the abdominal wall 140 leads to an increase in the size of the womb 142.

After this fixing has been done, a prenatal examination (not shown here) or a surgical intervention can be performed on the fetus 146 or on the womb 142 with the aid of medical instruments.

After the examination or surgical intervention has been performed, the draw-thread 152 is cut off, and a medical instrument 156 is guided through the abdominal wall 140 into the womb 142, by means of which the retrieval thread 154 of the anchor piece 150 located in the interior of the womb 142 is gripped. The anchor piece 150 is removed from the womb 142 through a shaft of the medical instrument 156 (FIG. 9, right). This introduction into the shaft is made easier by the retrieval thread 154 being applied at the end section of the anchor piece 130.

As can be seen from FIG. 6, the inner shaft 92 can house an ejection mechanism 125. This ejection mechanism 125 allows the anchor pieces 110 and 112 to be ejected laterally from the inner shaft 92 if the anchor pieces 110, 112 are prevented from falling off to the sides by tissue or tissue fluids. In the case shown, the ejection mechanism has two spring-loaded lugs 127 that can be driven out sideways. Such an ejection mechanism can also be provided in the embodiment in FIGS. 1 to 5. When inserting an anchor piece 110, 112 into recess 96, the lugs 127 are moved radially against the force of the spring. When inner shaft 92 is moved to the second position, the anchor pieces 110 and 112 are ejected laterally by the lugs 127.

What is claimed is:

1. A device for inserting at least one anchor piece into a hollow space of a living being, in order to fix a wall of said hollow space temporarily to a wall of a body of said human being by means of said anchor piece, comprising
    two shaft-like elements which are axially movable relative to one another along a longitudinal axis, wherein each of said two shaft-like elements has a jaw, and wherein one of said two shaft-like elements is designed as an outer tube having a distal end, and the other is designed as an axially displaceable inner shaft received in said outer tube, a distal end of said inner shaft is designed as a tip having a proximal end, said jaws being axially spaced apart along said longitudinal axis,
    at least one anchor piece having two axially spaced apart opposite ends, said at least one anchor piece can be held captive between said axially spaced apart jaws of said two shaft-like elements at said axially spaced apart opposite ends, wherein one of said jaws is arranged on said distal end of said outer tube, and the other one of said jaws is arranged on said proximal end of said tip of said inner shaft, wherein each of said jaws has at least one pocket, a shape of said pocket corresponds to a shape of one of said opposite ends of said anchor piece held by said pocket, wherein the at least one pocket of each of said jaws contacts a respective opposite end of said anchor piece to prevent radial movement of said anchor piece, and
    an actuating mechanism via which at least one of said two shaft-like elements can be moved in such a way that said anchor piece held between said two shaft-like elements can be released.

2. The device of claim 1, wherein said two shaft-like elements are designed and arranged in such a way that a recess is formed between them in which said at least one anchor piece can be held.

3. The device of claim 2, wherein said actuating mechanism has an actuating element for moving at least one of said two shaft-like elements, wherein, in a first position of said two shaft-like elements, said at least one anchor piece is held captive in said recess, and, in a second position of said two shaft-like elements, said at least one anchor piece can be fitted or released.

4. The device of claim 3, wherein said actuating mechanism has a spring which acts on said at least one shaft-like element in such a way that said shaft-like elements are brought into said first position.

5. The device of claim 4, wherein said actuating element, upon actuation counter to a force of said spring, moves said shaft-like elements in such a way that they are brought into the second position, and upon release of said actuating element, said shaft-like elements are brought back into said first position.

6. The device of claim 1, wherein a head is arranged on a proximal end of said two shaft-like elements.

7. The device of claim 6, wherein an actuating element designed as a push-button is arranged on said head.

8. The device of claim 7, wherein said actuating element is movable in a direction of an axial movement of said two shaft-like elements.

9. The device of claim 1, wherein said inner shaft is forced by means of a spring in a direction of a head arranged at a proximal end of said outer tube.

10. The device of claim 9, wherein said inner shaft is operatively connected to said actuating mechanism in such a way that an actuation of an actuating element causes an axial displacement of said inner shaft along a longitudinal axis.

11. The device of claim 2, wherein said recess is designed in such a way that two mutually opposite anchor pieces can be held in it.

12. The device of claim 11, wherein each jaw has two mutually opposite pockets.

13. The device of claim 9, wherein a mechanism for application of a trocar is arranged on said head.

14. The device of claim 1, wherein an ejection mechanism is provided for ejecting said at least one anchor piece.

15. The device of claim 1 further including an anchor piece, wherein said anchor piece has a body designed in the shape of a strip.

16. The anchor piece of claim 15, wherein said body is tubular shaped.

17. The anchor piece of claim 16, wherein one of the shaft-like elements is designed as an outer tube, and wherein said tube section of said body is designed as a same geometric shape of said outer tube.

18. The anchor piece of claim 15, wherein said anchor piece is rounded at both opposite ends.

19. The anchor piece of claim 15, wherein said anchor piece is provided with at least one approximately central opening for engagement of a draw-thread.

20. The anchor piece of claim 15, wherein said anchor piece is provided with at least one end opening for engagement of a retrieval thread.

* * * * *